United States Patent [19]
Cosyns et al.

[11] Patent Number: 6,072,091
[45] Date of Patent: Jun. 6, 2000

[54] PROCESS FOR SELECTIVE HYDROGENATION OF A HYDROCARBON CUT CONTAINING AT LEAST THREE CARBON ATOMS

[75] Inventors: Jean Cosyns, Maule; Blaise Didillon, Rueil Malmaison, both of France; Jean-Luc Nocca, Houston, Tex.; Etienne Lebas, Rueil Malmaison; Francoise Montecot, Les Clayes Sous Bois, both of France

[73] Assignee: Institut Francais du Petrole, Rueil-Malmaison Cedex, France

[21] Appl. No.: 08/894,691

[22] PCT Filed: Dec. 27, 1996

[86] PCT No.: PCT/FR96/02085

§ 371 Date: Aug. 26, 1997

§ 102(e) Date: Aug. 26, 1997

[87] PCT Pub. No.: WO97/24413

PCT Pub. Date: Jul. 10, 1997

[30] Foreign Application Priority Data

Dec. 27, 1995 [FR] France .................. 95 15530

[51] Int. Cl.⁷ .............. C07C 7/163; C07C 5/02
[52] U.S. Cl. ............ 585/259; 585/261; 585/264; 585/275; 585/277; 585/841; 208/144
[58] Field of Search .................. 585/258, 259, 585/261, 264, 275, 277, 841; 208/144

[56] References Cited

U.S. PATENT DOCUMENTS

| | | | |
|---|---|---|---|
| 4,847,430 | 7/1989 | Quang et al. | 568/697 |
| 5,059,732 | 10/1991 | Cosyns et al. | 585/259 |
| 5,306,852 | 4/1994 | Cosyns et al. | 585/254 |
| 5,368,691 | 11/1994 | Asselineau et al. | 203/29 |
| 5,461,178 | 10/1995 | Harandi | 585/259 |
| 5,595,634 | 1/1997 | Hearn et al. | 203/29 |
| 5,817,227 | 10/1998 | Mikitenko et al. | 208/143 |

FOREIGN PATENT DOCUMENTS

| | | |
|---|---|---|
| 0 556 025 | 8/1993 | European Pat. Off. . |
| 96 06900 | 3/1996 | WIPO . |

*Primary Examiner*—Bekir L. Yildirim
*Attorney, Agent, or Firm*—Millen, White, Zelano & Branigan, P.C.

[57] ABSTRACT

A process for the treatment of a feed comprising at least hydrocarbons containing at least 3 to 10 carbon atoms per molecule, including acetylenic and diolefinic hydrocarbons, comprises passing the feed into a distillation zone associated with a selective hydrogenation reaction zone comprising at least one catalytic hydrogenation bed which is internal to or external of the distillation zone, in which hydrogenation of at least a portion of the acetylenic and diolefinic hydrocarbons contained in the feed is carried out in the presence of a gas stream rich in hydrogen. The process is particularly suitable for the treatment of products from catalytic cracking.

21 Claims, 1 Drawing Sheet

PROCESS FOR SELECTIVE HYDROGENATION OF A HYDROCARBON CUT CONTAINING AT LEAST THREE CARBON ATOMS

FIELD OF THE INVENTION

This application is the national stage of PCT/FR96/02085, Dec. 27, 1996.

The invention concerns a process for the treatment of a feed partially constituted by hydrocarbons containing at least 3 carbon atoms per molecule, among them acetylenic and diolefinic hydrocarbons, also traces of arsine ($AsH_3$), carbonyl sulphide (COS) and alkylthiols (mercaptans). The process consists of treating the feed in a distillation column comprising a stripping zone and a rectification zone associated with a hydrogenation reaction zone comprising at least one catalytic bed in which at least a portion of the acetylenic and diolefinic compounds contained in the feed for (or to) the hydrogenation zone is hydrogenated, the feed being drawn off from at least one draw-off level and representing at least a portion of the liquid flowing in the rectification zone, at least a portion of the effluent from the reaction zone being reintroduced into the rectification zone to ensure continuity of distillation so as to produce an effluent from the head of the distillation column which is highly depleted in acetylenic and diolefinic hydrocarbons containing at most 5 carbon atoms, and an effluent from the bottom of the distillation column which is also depleted in these compounds.

The process of the invention can also affect addition of light alkylthiols (methyl mercaptan and ethyl mercaptan) in the reaction zone to diolefinic hydrocarbons containing at most 5 carbon atoms, producing heavy thioethers containing at least 5 carbon atoms and boiling in the range of hydrocarbons containing at least 6 carbon atoms. The effluent from the reaction zone is reintroduced into the rectification zone so as to produce an effluent from the head of the rectification zone which is highly depleted in light alkylthiols and an effluent from the bottom of the distillation column which comprises thioethers containing at least 5 carbon atoms.

BACKGROUND OF THE INVENTION

Various processes used in the oil industry, such as thermal cracking, coking, visbreaking, catalytic cracking and steam cracking, produce large quantities of light olefinic hydrocarbon cuts which also contain acetylenic and diolefinic hydrocarbons.

The subsequent uses of these olefsins in the manufacture of polymers or fuel, for example, require selective elimination of the acetylenic and diolefinic hydrocarbons which is as complete as possible.

The usual technique for such purification is selective hydrogenation carried out in a stream of hydrogen in a reactor comprising a fixed bed of a catalyst constituted by a metal from group VIII. The feed, which arrives at ambient temperature, is generally pumped and reheated and reintroduced into the hydrogenation reactor. The hydrogen required is added in any suitable fashion. At the reactor outlet, the excess hydrogen and the gaseous hydrocarbons contained in the supply gas are removed from the liquid hydrocarbon-containing gas in any suitable fashion, generally in a separator drum followed, if necessary, by a topping column.

European patent application EP-A 1-0 556 025 recently described a process for selective hydrogenation of diolefins in a light olefinic hydrocarbon refinery cut. In this technology, hydrogenation of the diolefin is internal of the rectification zone of the distillation column, the catalyst itself acting as a distillation structure. This mode of operation economises on equipment. However in this type of technology, where the reaction and distillation proceed simultaneously in the same physical space, the liquid phase descends through the whole catalytic bed in the reaction zone in rivulets or streams of liquid. The gas phase containing the vaporised fraction of the feed and hydrogen rises through the catalytic bed in columns of gas. Since the hydrogen necessary for reaction is in the gas phase, hydrogenation occurs essentially in that phase on the portion of the catalyst in contact with the fraction of hydrocarbons which is in the gas phase.

In that technology, then, the lightest hydrocarbons are preferentially hydrogenated. Thus in the cited patent application, the hydrocarbons containing five carbon atoms contained in the gasoline, which also comprises hydrocarbons containing at least 6 carbon atoms, are hydrogenated. The hydrogenation reaction is carried out in the rectification zone of the depentaniser. Thus the diolefins present in the $C_5$ cut which go into the gas phase are preferentially hydrogenated.

Such a technology cannot be put into practice on a general basis and in some cases has such disadvantages as to render it impracticable. Thus, for example, in the catalytic cracking process intended to produce gasoline from heavy petroleum fractions, the production of a large quantity of essentially olefinic gaseous hydrocarbons which also contain small percentages of diolefins cannot be avoided.

In the most general mode for separating catalytic cracking products, "primary" fractionation is first carried out to separate the products from the reaction section for cracking light gases into liquefiable gases mixed with gasoline and into products which are heavier than gasoline. The core fraction, which generally contains hydrocarbons containing at least three carbon atoms to hydrocarbons containing ten carbon atoms, is then sent to a debutaniser which separates the gasoline at the bottom and the mixture of hydrocarbons containing three and four carbon atoms which is generally very rich in propylene and butenes and contains small quantities of diolefins, mainly butadiene. The mixture also contains numerous impurities, such as carbonyl sulphide (COS) and methylthiol ($CH_3SH$), and very often traces of arsine ($AsH_3$). Such impurities strongly deactivate the hydrogenation catalyst when the latter operates on the above mixture and thus an initial purification treatment must be carried out to eliminate arsine and COS. As a result, the process described in European patent application EP-A1-0 556 025, which consists of placing the catalyst in a rectification zone which sees the simultaneous passage of the descending liquid phase and the ascending gas phase, cannot be carried out as the catalyst will be poisoned by $AsH_3$ and COS present mainly in the gas phase, their boiling points being respectively –55° C. and –50° C.

SUMMARY OF THE INVENTION

The process of the invention can avoid the severe disadvantages described above. It consists of treating the cut from the cracking process, comprising hydrocarbons containing 3 to 10 carbon atoms, among them generally small proportions of acetylenic and diolefinic hydrocarbons, also traces of arsine ($AsH_3$), carbonyl sulphide (COS) and alkylthiols (mercaptans), in a distillation column comprising a rectification zone in communication associated with a hydrogenation reaction zone constituted by at least one catalytic bed, in which at least a portion of the acetylenic and diolefinic hydrocarbons contained in said cut is hydrogenated in the presence of a gas stream which is rich in hydrogen. The feed for the reaction zone is drawn off at a draw-off plate and represents the major portion of the liquid flowing in the rectification zone and, preferably, flowing at an intermediate level in the rectification zone, the major portion of the effluent from the reaction zone being reintroduced into the rectification zone so as to ensure continuity of distillation and, finally, to remove an effluent which is highly depleted in acetylenic and/or diolefinic hydrocarbons containing at most 5 carbon atoms from the head of the distillation column and an effluent which is also depleted in these compounds from the bottom of the distillation column.

The distillation column generally comprises rectification contact means selected from the group formed by plates, bulk packing and structured packing, as is known to the skilled person, so that the overall efficiency is generally at least five theoretical plates.

The hydrogenation reaction zone generally comprises at least one catalytic hydrogenation bed, preferably 1 to 4 catalytic beds; when it comprises at least two catalytic beds, these beds can be separated by at least one rectification contact means. The hydrogenation reaction zone carries out at least partial hydrogenation of acetylenic and diolefinic compounds comprising 3 to 5 carbon atoms, present in the feed such that the concentration of these compounds is below a certain value which is set in advance.

In a first implementation of the invention, the process is such that the hydrogenation reaction zone is at least partially, preferably completely, internal to the distillation column. Thus for the portion of the reaction zone which is internal to the distillation column, the liquid is drawn off naturally by flow in the portion of the reaction zone which is internal to the distillation column, and reintroduction of liquid to the distillation column is also natural by liquid flow from the reaction zone internal to the distillation column. Further, the process of the invention is preferably carried out so that the flow of the liquid to be hydrogenated is co-current with the flow of the gas stream comprising hydrogen for every catalytic bed in the internal portion of the hydrogenation zone and so that the distillation vapour is separated from said liquid for every catalytic bed in the internal portion of the hydrogenation zone.

In a second implementation of the invention, which is independent of the preceding implementation, the process is such that the hydrogenation reaction zone is at least partially, preferably completely, external to the distillation column. Thus the effluent from at least one catalytic bed in the external portion of the hydrogenation zone is generally reintroduced in close proximity to a draw-off level, preferably to the draw-off level which supplied said catalytic bed. In general, the process of the invention comprises 1 to 4 draw-off level(s) which feed the external portion of the hydrogenation zone. There are thus two possible cases. In the first case, the external portion of the hydrogenation zone is supplied by a single draw-off level and thus if said portion comprises at least two catalytic beds distributed in at least two reactors, said reactors are disposed in series or in parallel. In the second, preferred, case, the external portion of the hydrogenation zone is supplied by at least two draw-off levels.

In a third implementation, which combines the two implementations described above, the process of the invention is such that the hydrogenation zone is both partially incorporated in the distillation column, i.e., internal to the distillation column, and partially external to the distillation column. In such an implementation, the hydrogenation zone comprises at least two catalytic beds, at least one catalytic bed being internal to the distillation column, and at least one other catalytic bed being external to the distillation column. When the external portion of the hydrogenation zone comprises at least two catalytic beds, each catalytic bed is supplied by a single draw-off level, preferably associated with a single level where the effluent from said catalytic bed in the external portion of the hydrogenation zone is reintroduced, said draw-off level being distinct from the draw-off level which supplies the other catalytic bed(s). In general, the liquid to be hydrogenated firstly circulates either partially or completely in the external portion of the hydrogenation zone, then in the internal portion of said zone. The portion of the reaction zone which is internal to the distillation column has the characteristics described in the first implementation. The portion of the reaction zone which is external to the distillation column has the characteristics described in the second implementation.

In a further implementation of the invention, which may or may not be independent of the preceding implementations, the process of the invention is such that the flow of liquid to be hydrogenated is co-current or counter-current, preferably co-current, with respect to the flow of the gas stream comprising hydrogen, for every catalytic bed in the hydrogenation zone.

In order to carry out the hydrogenation of the process of the invention, the theoretical hydrogen molar ratio necessary for the desired conversion of the acetylenic and diolefinic hydrocarbons is 1. The quantity of hydrogen distributed in the gas stream, before or in the hydrogenation zone, is general slightly in excess with respect to this stoichiometry to take into account the fact that hydrogenation is not perfectly selective and that a small portion of the olefsins present is also hydrogenated. Further, some hydrogen may pass through the catalytic zone without being consumed. This excess hydrogen, if it exists, can advantageously be recovered, either by compression and re-use in the hydrogenation zone, or by sending it to a further installation which uses hydrogen.

The hydrogen used in the process of the invention may originate from any source producing hydrogen which is at least 50% pure, preferably at least 80% pure and more preferably at least 90% pure. As an example, hydrogen from catalytic reforming processes, methanation processes, PSA (pressure swing adsorption), electrochemical generation, steam cracking or steam reforming can be cited.

Generally, and preferably, the operating conditions are carefully selected with respect to the nature of the feed and other parameters which are known to the distillation specialist such as the distillate/feed ratio, so that the overhead effluent from the distillation column is practically free of acetylenic and diolefinic hydrocarbons containing at most 5 carbon atoms.

In accordance with the technology of the invention, the catalyst is disposed such that the reaction and distillation proceed independently and consecutively, as is taught in, for example, U.S. Pat. Nos. 4,847,430, 5,130,102 and U.S. Pat. No. 5,368,691, the vapour from the distillation column not in practice traversing any catalytic bed in the reaction zone. Thus the process of the invention is generally such that the flow of the liquid to be hydrogenated is co-current with the flow of the gas stream comprising hydrogen and such that the distillation vapour is substantially not in contact with the catalyst (which generally means that, in practice, said vapour is separated from said liquid to be hydrogenated) for every catalytic bed in the internal portion of the hydrogenation zone. In the technology of the invention, every catalytic bed in the portion of the reaction zone which is in the distillation column is generally such that the gas stream comprising hydrogen and the liquid stream which is to react circulate co-currently, generally upwardly, through said bed, even if overall in the catalytic distillation column, the gas stream comprising hydrogen and the liquid stream which is to react circulate in a counter-current. Such systems generally comprise at least one liquid distribution means, for example a liquid distributor, in every catalytic bed in the reaction zone. Nevertheless, when these technologies have been designed for catalytic reactions occurring between liquid reactants, without modification they may not be suitable for a catalytic hydrogenation reaction where one of the reactants, hydrogen, is in the gaseous state. For every catalytic bed in the internal portion of the hydrogenation zone, it is thus generally necessary to add an apparatus for distributing a gas stream comprising hydrogen, for example using one of the three techniques described below. Thus the internal portion of the hydrogenation zone comprises at least one liquid distribution apparatus and at least one means for distributing a gas stream comprising hydrogen for every catalytic bed in the internal portion of the hydrogenation zone. In a first technique, the apparatus for distributing a gas stream comprising hydrogen is disposed upstream of the liquid distribution apparatus and thus upstream of the catalytic bed. In a second technique, the apparatus for distributing a gas stream comprising hydrogen is disposed at the level of the liquid distribution apparatus, such that the gas stream comprising hydrogen is introduced into the liquid upstream of the catalytic bed. In a third technique, the apparatus for distributing a gas stream comprising hydrogen is disposed downstream of the liquid distribution apparatus, and thus in the catalytic bed, preferably not far from said liquid distribution apparatus in said catalytic bed. The terms "upstream" and "downstream" used above are with respect to the direction of circulation of liquid which traverses the catalytic bed, i.e., generally upwardly.

In one preferred implementation of the process of the invention, the catalyst in the internal portion of the hydrogenation zone is disposed in the distillation zone using the basic apparatus described in U.S. Pat. No. 5,368,691, arranged so that every catalytic bed internal to the distillation column is supplied by a gas stream comprising hydrogen, regularly distributed at its base, for example using one of the three techniques described above. Using this technology, if the hydrogenation zone is completely internal to said column, the catalyst in every catalytic bed, internal to the distillation column, is then in contact with an ascending liquid phase, generated by the reflux introduced to the top of the distillation column, and with the gas stream comprising hydrogen which circulates in the same direction as the liquid; contact with the vapour phase from distillation is prevented by causing the latter to be transported by at least one specially provided chimney.

When the hydrogenation zone is at least partially internal to the distillation column, the operating conditions in the portion of the hydrogenation zone which is internal to the distillation column are linked to the distillation operating conditions. Distillation is carried out such that its bottoms product preferably contains the major portion of the hydrocarbons containing at least 5 carbon atoms. It is carried out at a pressure which is generally in the range 2 to 25 bar, preferably 4 to 15 bar (1 bar=$10^5$ Pa), with a reflux ratio which is in the range 0.5 to 10, preferably in the range 3 to 6. The temperature at the head of the zone is generally in the range 20° C. to 100° C. and the temperature at the bottom of the zone is generally in the range 100° C. to 300° C. The hydrogenation reaction is carried out under conditions which are generally intermediate between those at the head and those at the bottom of the distillation column, at a temperature which is in the range 50° C. to 150° C., preferably in the range 60° C. to 100° C., and at a pressure which is in the range 2 to 20 bar, preferably in the range 5 to 15 bar. The liquid to be hydrogenated is supplied with a gas stream comprising hydrogen at a flow rate which depends on the concentration of acetylenic and diolefinic hydrocarbons containing at most 5 carbon atoms per molecule in the feed to the distillation column. It is generally at least equal to the flow rate corresponding to the stoichiometry of the hydrogenation reactions taking place and at most equal to the flow rate corresponding to 5 times the stoichiometry, preferably in the range 1 to 3 times the stoichiometry.

When the hydrogenation zone is partially external to the distillation column, the catalyst disposed in said external portion is present using any technology known to the skilled person under the operating conditions (temperature, pressure, . . . ), which may or may not be independent and are preferably independent, of the operating conditions of the distillation column.

In the portion of the hydrogenation zone which is external to the distillation column, the operating conditions are generally as follows: the pressure required for this hydrogenation step is generally in the range 1 to 60 bar, preferably between 2 and 25 bar. The operating temperature of the external portion of the hydrogenation zone is generally in the range 50° C. to 150° C., preferably in the range 60° C. to 120° C. The space velocity in the external portion of said hydrogenation zone, calculated with respect to the catalyst, is generally in the range 1 to 50, more particularly between 1 and $30^{-1}$(volume of feed per volume of catalyst per hour). The hydrogen flow rate corresponding to the stoichiometry of the hydrogen reactions taking place is in the range 0.5 to 10 times said stoichiometry, preferably between 1 and 3 times said stoichiometry. Within the context of the process of the invention, however, the temperature and pressure conditions can also be between those which are established at the head and bottom of the distillation column.

More generally, depending on the position of the hydrogenation zone in the process of the present invention, the catalyst generally comprises at least one metal selected from group VIII deposited on a support.

The catalyst is preferably a palladium catalyst.

In particular, catalysts sold by PROCATALYSE under the trade names LD 265® a and LD277-3® are used.

The following example illustrates the invention.

BRIEF DESCRIPTION OF THE DRAWINGS

The attached FIGURE is a schematic flowsheet of an embodiment of the invention.

EXAMPLE

Figure 1:
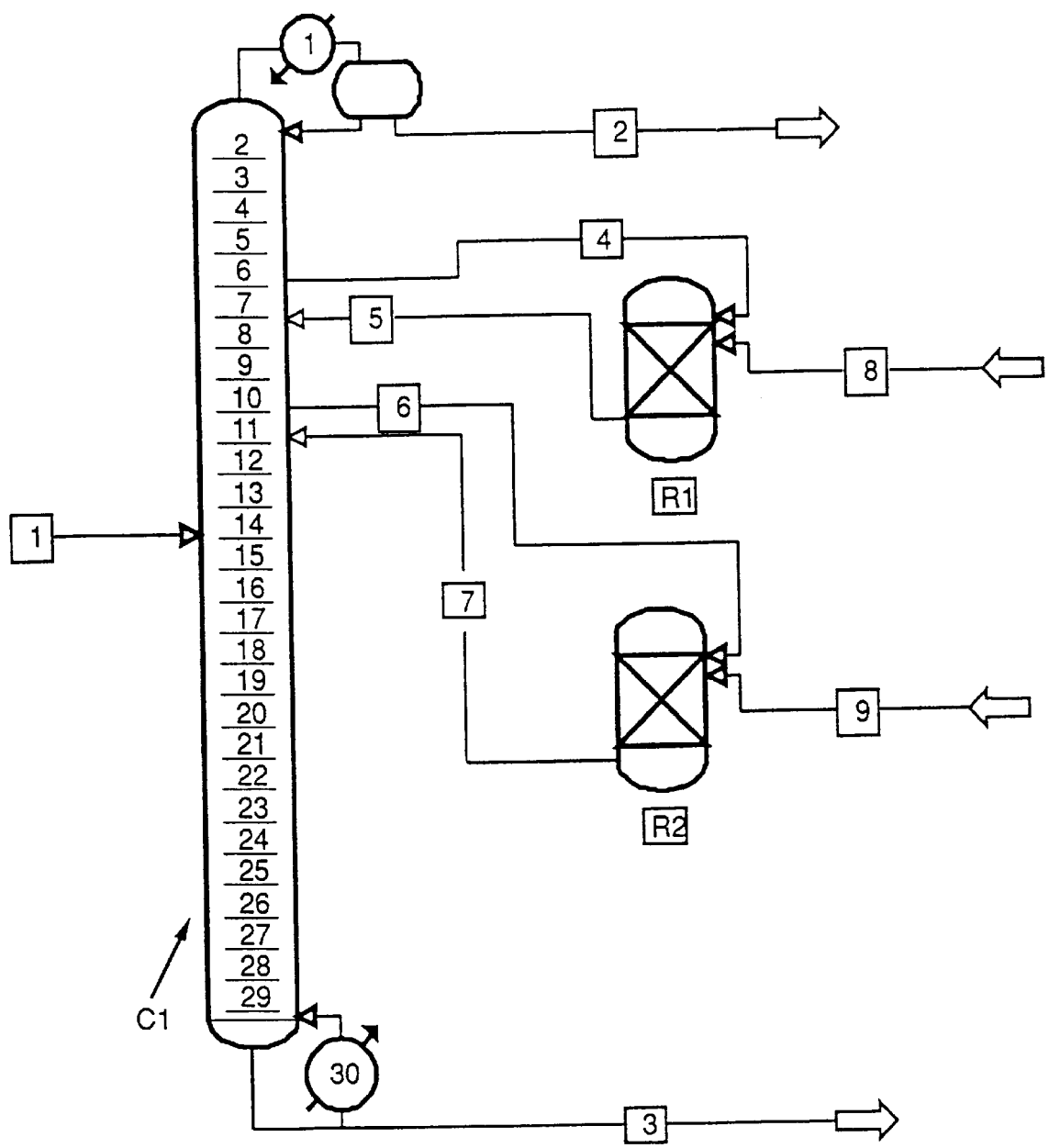

The example used the process scheme shown in the FIGURE.

A cut from a catalytic cracking unit was introduced into a distillation and reaction zone constituted by a column C1, comprising 30 theoretical plates (including condenser 1 and reboiler 30). Supply was via line 1 to plate 14.

The reactive distillation unit comprised two hydrogenation zones R1 and R2 external to the column.

Hydrogenation zones R1 and R2 were supplied by sidestreams extracted from plates 6 and 10 respectively via lines 4 and 6; the effluent from each of the external reactors was reintroduced to the plate below the extraction plate supplying the external reactor under consideration, i.e., plates 7 and 11 respectively, via lines 5 and 7. The two reactors each contained a palladium catalyst sold by PROCATALYSE under the trade name LD-265®. They each received a hydrogen stream, via lines 8 and 9 respectively.

The overhead effluent from column C1 was evacuated via line 2 after condensing, and the bottom effluent was evacuated via line 3.

The operating conditions were as follows:

supply flow rate to column C 1: 2146.84 kmol/h;

column head pressure: 1 1.3 bars absolute;

column bottom pressure: 11.5 bars absolute;

column supply temperature: 111° C.;

column head temperature: 44° C.;

column bottom temperature: 170° C.;

temperature of reactor R1: 73° C.;

flow rate in reactor R1: 1200 kmole/h;

temperature of reactor R2: 87° C.;

flow rate in reactor R2: 1000 kmole/h.

With this configuration and under these operating conditions, the process gave the following results:

TABLE 1

|  | Feed (mol %) | Head (mol %) | Bottom (mol %) |
| --- | --- | --- | --- |
| $H_2O$ | 0.0002 | 0.0006 | 0 |
| $N_2$ | 0 | 0 | 0 |
| CO | 0 | 0 | 0 |
| $CO_2$ | 0 | 0 | 0 |
| $H_2S$ | 0.0433 | 0.1233 | 0 |
| $H_2$ | 0 | 0 | 0 |
| C1 | 0 | 0 | 0 |
| C2 | 0.0251 | 0.0715 | 0 |
| Ethylene | 0.0003 | 0.0007 | 0 |
| C3 | 16.9195 | 48.1552 | 0.0001 |
| iC4 | 3.9905 | 11.2647 | 0.0488 |
| nC4 | 1.6451 | 4.1906 | 0.2326 |
| 1-butene | 12.8531 | 35.6012 | 0.5067 |
| iC5 | 5.6754 | 0.3211 | 8.491 |
| nC5 | 1.1646 | 0.0178 | 1.7941 |
| Cyclopentane | 0.3013 | 0.0001 | 0.4668 |
| 1-pentene | 12.6208 | 0.1716 | 19.5755 |
| 50–70 | 10.6238 | 0 | 16.4159 |
| 70–90 | 9.1166 | 0 | 14.0859 |
| 90–110 | 7.7906 | 0 | 12.0372 |
| 110–130 | 6.6165 | 0 | 10.223 |
| 130–140 | 2.9066 | 0 | 4.4909 |
| 140–150 | 2.6237 | 0 | 4.0538 |
| 150–160 | 2.239 | 0 | 3.4594 |
| 160–170 | 1.6277 | 0 | 2.5150 |
| 170–180 | 0.7715 | 0 | 1.1921 |
| 180–190 | 0.2092 | 0 | 0.3232 |
| 190–200 | 0.0425 | 0 | 0.0656 |
| 200–210 | 0.0076 | 0 | 0.0118 |
| 210–220 | 0.0012 | 0 | 0.0018 |
| 220–230 | 0.0001 | 0 | 0.0002 |
| 230–250 | 0 | 0 | 0 |
| 250–270 | 0 | 0 | 0 |
| 270–290 | 0 | 0 | 0 |
| 1,2-butadiene | 0 | 0 | 0 |
| 1,3-butadiene | 0.1845 | 0.0816 | 0.0087 |
| Flow rate (kmol/h) | 2146.84 | 754.156 | 1389.46 |

80% conversion of butadiene was obtained. Further, the 1,3-butadiene concentration in the overhead product from the column was 800 ppm by moles.

We claim:

1. A process for selectively hydrogenating at least one of acetylenic and diolefinic hydrocarbons present in a feed comprising hydrocarbons of from 3–10 carbon atoms, said process comprising:

at a feedpoint, passing said feed into a distillation zone including a rectifying zone, wherein liquid flows therein;

drawing off at least one intermediate level of the rectifying zone at least one side stream representing a major portion of the liquid flowing in the rectification section zone at said level;

sending said at least one side stream to at least one separate selective hydrogenation reaction zone comprising at least one catalytic bed being fed with a gas stream rich in hydrogen so as to produce a hydrogenated effluent, said at least one selective hydrogenation zone being at least partially internal to and in communication with the distillation zone;

introducing at least a major portion of the hydrogenated effluent of said at least one selective hydrogenation reaction zone into the rectifying section of the distillation zone to ensure continuity of the distillation; and recovering a distillate highly depleted in acetylenic and/or diolefinic hydrocarbons at the head of the distillation zone and, at the bottom of the distillation zone, a residue depleted in acetylenic and/or diolefinic hydrocarbons, with the provision that vapor in the distillation zone is maintained out of contact with all selective hydrogenation reaction zones.

2. A process according to claim 1, wherein the acetylenic and/or diolefinic hydrocarbons to be selectively hydrogenated contain at most 5 carbon atoms, said process conducted so as to cause an effluent which is highly depleted in acetylenic and/or diolefinic hydrocarbons containing at most 5 carbon atoms to leave the head of the distillation column and an effluent which is also depleted in said acetylenic and/or olefinic compounds to leave the bottom of the distillation column.

3. A process according to claim 1, characterized in that said at least one selective hydrogenation zone comprises 1 to 4 catalytic beds.

4. A process according to claim 1, characterized in that the selective hydrogenation zone in communication with the distillation zone is completely internal to said distillation zone.

5. A process according to claim 1, comprising at least two selective hydrogenation reaction zones, at least one zone being internal to the distillation zone and at least one other zone being external of said distillation zone.

6. A process according to claim 1, characterized in that the catalyst is a supported catalyst comprising at least one noble metal from group VIII.

7. A process according to claim 6, characterized in that the catalyst is a palladium catalyst.

8. A process according to claim 3, wherein the acetylenic and/or diolefinic hydrocarbons to be selectively hydrogenated contain at most 5 carbon atoms, said process conducted so as to cause an effluent which is highly depleted in said acetylenic and/or diolefinic hydrocarbons containing at most 5 carbon atoms to leave the head of the distillation column and an effluent which is also depleted in said acetylenic and/or olefinic compounds to leave the bottom of the distillation column.

9. A process according to claim 2, wherein the acetylenic and/or diolefinic hydrocarbons to be selectively hydrogenated contain at most 5 carbon atoms, said process conducted so as to cause an effluent which is highly depleted in acetylenic and/or diolefinic hydrocarbons containing at most 5 carbon atoms to leave the head of the distillation column and an effluent which is also depleted in said acetylenic and/or olefinic compounds to leave the bottom of the distillation column.

10. A process according to claim 2, characterized in that the selective hydrogenation zone in communication with the distillation zone is internal to said distillation zone.

11. A process according to claim 2, characterized in that the selective hydrogenation zone in communication with the distillation zone is external to said distillation zone.

12. A process according to claim 1, comprising at least two selective hydrogenation reaction zones, at least one selective hydrogenation zone being internal to the distillation zone and at least one other selective hydrogenation zone being external of said distillation zone.

13. A process according to claim 8, characterized in that the selective hydrogenation zone in communication with the distillation zone is internal to said distillation zone.

14. A process according to claim 8, characterized in that the selective hydrogenation zone in communication with the distillation zone is external to said distillation zone.

15. A process according to claim 8, comprising at least two selective hydrogenation reaction zones, at least one selective hydrogenation zone being internal to the distillation zone and at least one other selective hydrogenation zone being external of said distillation zone.

16. A process according to claim 9, characterized in that the selective hydrogenation zone in communication with the distillation zone is internal to said distillation zone.

17. A process according to claim 9, characterized in that the selective hydrogenation zone in communication with the distillation zone is external to said distillation zone.

18. A process according to claim 9, comprising at least two selective hydrogenation reaction zones, at least one selective hydrogenation zone being internal to the distillation zone and at least one other selective hydrogenation zone being external of said distillation zone.

19. A process according to claim 1, comprising at least two of said side streams, each side stream being passed to a separate selective hydrogenation zone.

20. A process according to claim 1, wherein said at least one side stream is removed from the distillation zone at above the feedpoint.

21. A process according to claim 1, wherein all side streams are removed from the distillation zone at above the feedpoint.

* * * * *